US009536193B1

(12) United States Patent
Labrie et al.

(10) Patent No.: US 9,536,193 B1
(45) Date of Patent: Jan. 3, 2017

(54) MINING BIOLOGICAL NETWORKS TO EXPLAIN AND RANK HYPOTHESES

(71) Applicant: International Business Machines Corporation, Armonk, NY (US)

(72) Inventors: Jacques J. Labrie, Sunnyvale, CA (US); Pathirage D. Perera, Fairborn, OH (US); Meenakshi Nagarajan, San Jose, CA (US); Cartic Ramakrishnan, San Jose, CA (US); William Scott Spangler, San Martin, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 14/964,530

(22) Filed: Dec. 9, 2015

(51) Int. Cl.
 *G06N 5/00* (2006.01)
(52) U.S. Cl.
 CPC ..................... *G06N 5/003* (2013.01)
(58) Field of Classification Search
 None
 See application file for complete search history.

(56) References Cited

U.S. PATENT DOCUMENTS

| 8,594,942 | B2 | 11/2013 | Allen et al. | |
|---|---|---|---|---|
| 2002/0087275 | A1 | 7/2002 | Kim et al. | |
| 2005/0197783 | A1 | 9/2005 | Kuchinsky et al. | |
| 2010/0063948 | A1* | 3/2010 | Virkar .................... | G06N 3/02 706/12 |
| 2014/0046776 | A1* | 2/2014 | Kanigsberg ....... | G06F 17/30867 705/14.66 |
| 2014/0280224 | A1 | 9/2014 | Feinberg et al. | |
| 2014/0288910 | A1 | 9/2014 | Chandra et al. | |
| 2014/0351289 | A1 | 11/2014 | Bekas et al. | |
| 2015/0024951 | A1 | 1/2015 | Chen et al. | |
| 2015/0119289 | A1* | 4/2015 | Chen ...................... | G06F 19/12 506/24 |
| 2016/0092631 | A1* | 3/2016 | Yandell ................... | G06F 19/22 702/19 |

OTHER PUBLICATIONS

Ullah et al., Estimating a Ranked List of Human Genetic Diseases by Associating Phenotype-Gene with Gene-Disease Bipartite Graphs, Jul. 2015, ACM Trans. Intell. Syst. Technol. 6, 4, Article 56, pp. 1-21.*

(Continued)

*Primary Examiner* — Alan Chen
(74) *Attorney, Agent, or Firm* — VanLeeuwen & VanLeeuwen; Diana R. Gerhardt

(57) ABSTRACT

An approach is provided to identify important paths in a biological relationship graph for exploration by researchers. In the approach, a biological meaningfulness analysis is performed on the biological relationship graph that has a number of paths through the graph formed by a number of connected nodes. The biological meaningfulness analysis is based on a process similarity calculation of gene ontologies of the nodes in the paths and a contextual similarity calculation of word occurrences from documents in a corpus where a reference to the respective nodes are found. A biological interestingness analysis is also performed on the biological relationship graph. The paths are screened based on the meaningfulness analysis and the interestingness analysis. The screened data is displayed to the user.

17 Claims, 9 Drawing Sheets

(56) References Cited

OTHER PUBLICATIONS

Wei et al., Mining Biomedical Literature and Ontologies for Drug Repositioning Discovery, 2014, Springer International Publishing Switzerland, pp. 373-384.*
Pivovarov et al., A hybrid knowledge-based and data-driven approach to identifying semantically similar concepts, 2012, Journal of Biomedical Informatics, 45, pp. 471-481.*
S. Yu et al., Kernel-based Data Fusion for Machine Learning, Chapter 5: Multi-view Text Mining for Disease Gene Prioritization and Clustering, 2011, Springer-Verlab Berlin Heidelberg, SCI 345, pp. 109-144.*
Nakazawa et al.,"Integrated Visualization of Gene Network and Ontology Applying a Hierarchical Graph Visualization Technique," 2012 16th International Conference on Information Visualization (IV), Jul. 2012, IEEE Computer Society, Montpellier, France, pp. 81-86.

* cited by examiner

MINING BIOLOGICAL NETWORKS TO EXPLAIN AND RANK HYPOTHESES

BACKGROUND

Biologists have generated huge amount of knowledge over the centuries. The availability of this knowledge in digital format presents the potential of discovering new knowledge by mining existing knowledge. However, it is known that biological events are results of complex interactions between multiple entities. Because of the vast amount of information, coupled with the complex interactions found between entities referenced in the information, identifying new areas of discovery in biological fields is increasingly difficult.

BRIEF SUMMARY

An approach is provided to identify important paths in a biological relationship graph for exploration by researchers. In the approach, a biological meaningfulness analysis is performed on the biological relationship graph that has a number of paths through the graph formed by a number of connected nodes. The biological meaningfulness analysis is based on a process similarity calculation of gene ontologies of the nodes in the paths and a contextual similarity calculation of word occurrences from documents in a corpus where a reference to the respective nodes are found. A biological interestingness analysis is also performed on the biological relationship graph. The interestingness analysis is based on a path diversity value calculated for each of the paths and a path rarity value calculated for each of the paths. The path diversity value is based on a number of distinct documents in each of the paths and the number of connections in the respective paths, while the path rarity value is based a total degrees of the nodes that form the paths. The paths are then screened based on the biological meaningfulness analysis and the biological interestingness analysis. The screened data is displayed to a user, such as a biology researcher.

The foregoing is a summary and thus contains, by necessity, simplifications, generalizations, and omissions of detail; consequently, those skilled in the art will appreciate that the summary is illustrative only and is not intended to be in any way limiting. Other aspects, inventive features, and advantages of the present disclosure, as defined solely by the claims, will become apparent in the non-limiting detailed description set forth below.

BRIEF DESCRIPTION OF THE SEVERAL VIEWS OF THE DRAWINGS

The present disclosure may be better understood, and its numerous objects, features, and advantages made apparent to those skilled in the art by referencing the accompanying drawings, wherein.

DETAILED DESCRIPTION

Figure 1:
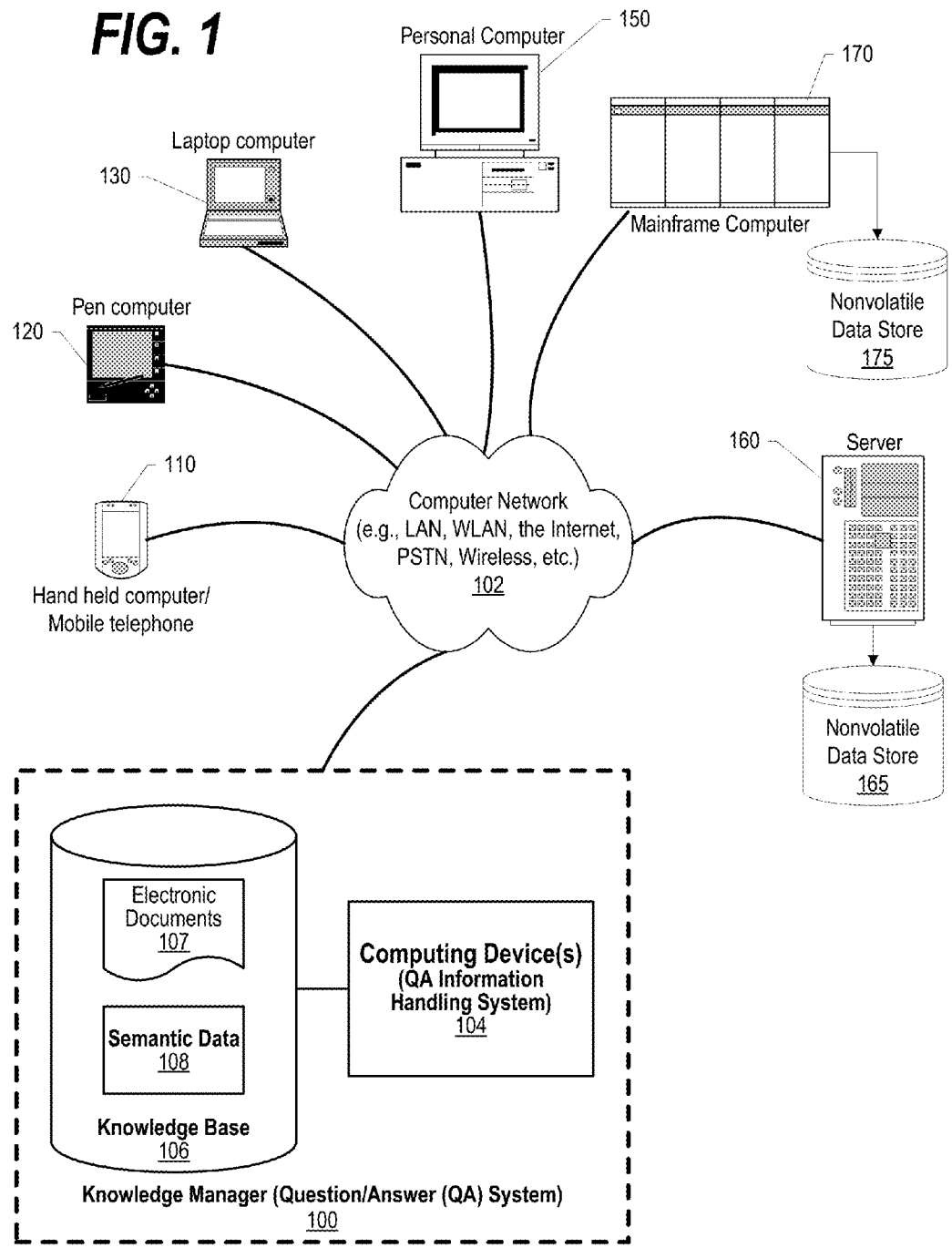
FIG. 1 depicts a schematic diagram of one illustrative embodiment of a question answering (QA) system in a computer network.

FIGS. 1-9 depict an approach that uses a biological relationship graph and a corpus of biological information to provide meaningful and interesting biological paths to researchers for further exploration and research. Biologists have generated huge amount of knowledge over the centuries. The availability of this knowledge in digital format presents the potential of discovering new knowledge by mining existing knowledge with computational techniques. Over the years scientists have worked on developing techniques to generate new hypotheses for given problem using the existing biological knowledge. However, majority of these techniques find hypotheses which state the correlation between two biological entities. However, it is known that biological events are not typically a results of interaction between two entities rather complex interactions between multiple entities. It is crucial to understand this complex interactions of multiple entities in order to understand the diseases and develop/re-purpose drugs for them.

The approach disclosed herein focuses on providing more than correlations in data to discover promising explanations for given biological events in the form of biological paths. These biological paths are rank based on both meaningfulness interestingness. The algorithm disclosed herein receives multiple biological entities of interest as input, finds paths between them, and ranks the paths based on their biological meaningfulness and interestingness.

The algorithm used in this approach uses biological knowledge in the form of a graph as an input to the algorithm. The nodes of the graph are biological entities such as genes, drugs, and conditions, while the edges of the graph are the interactions between the nodes. For example, one node might be a particular disease and another node might be a particular gene, with the interaction being that the particular gene "causes" the particular disease. In another example, one node might be a particular drug and another node might be a particular disease, with the interaction being that the particular drug "treats" the particular disease.

Given the multiple entities of interest, the approach first find paths between the nodes in the graph and ranks these paths based on (1) biological meaningfulness, and (2) biological interestingness. Below is one embodiment of a ranking strategy that can be employed.

First, paths are ranked based on biological meaningfulness. Here, two heuristics are used to capture the biological meaningfulness. (1) the nodes on the paths should be involved in similar biological processes (process similarity), and (2) the nodes on the path should be discussed in a similar context (contextual similarity).

For process similarity, the process similarity of nodes is captured by their Gene Ontology (GO) annotations. Each node is represented as a vector of GO annotations weighted by their term frequency-inverse document frequency (TFIDF) values. TFIDF is a numerical statistic that is intended to reflect how important a word is to a document in a collection or corpus. The TFIDF value increases proportionally to the number of times a word appears in the document, but is offset by the frequency of the word in the corpus, which helps to adjust for the fact that some words appear more frequently in general. The process similarity of two nodes is calculated by the cosine similarity of two vectors. Below is an example of GO data for two nodes:

| GO Annotations: | | | | |
| --- | --- | --- | --- | --- |
| GO1 (idf = 0.89) | GO2 (idf = 0.12) | GO3 (idf = 0.98) | GO4 (idf = 0.97) | ... GOn (idf = 0.72) |
| gene1: | | | | |
| 0 | 0.12 | 0.98 | 0 | ... 0 |
| gene2: | | | | |
| 0 | 0 | 0.98 | 0 | ... 0.72 |

Process similarity = cosine similarity (gene1, gene2)

In one embodiment, the contextual similarity of the entities are captured by the bag of words model that has been developed based on the Medline articles. In this embodiment, each node is represented as a vector of words weighted by the their TFIDF values in the Medline corpus. The contextual similarity is calculated by the cosine similarity of these two vectors. Below is an example of set of word data for two nodes:

| Words: | | | | |
| --- | --- | --- | --- | --- |
| word1 (idf = 0.73) | word2 (idf = 0.65) | word3 (idf = 0.02) | word4 (idf = 0.97) | ... Wordn (idf = 0.52) |
| node 1: | | | | |
| 0 | 1.95 | 0.02 | 0 | ... 0 |
| node 2: | | | | |
| 1.46 | 0 | 0.24 | 0 | ... 0.52 |

Contextual similarity = cosine similarity (entity1, entity2)

The above two similarity measures are calculated for each component in the path (with a component being the interaction between two nodes (in other words it is a triple). A path consists of multiple such components). These values are aggregated. Paths formed by components with higher process similarity and contextual similarity are ranked higher. The following equation captures this idea:

Meaningfulness value of path component=($\frac{1}{2}$)(process similarity+contextual similarity)*(1−|process similarity−contextual similarity|)

Meaningfulness of the path=$(1/n)\Sigma_{i=1,n}$(meaningfulness of component$_i$)

In one embodiment, the paths that exceed a predetermined threshold value for the meaningfulness value are selected for the next step of ranking based on interestingness. In this embodiment, the threshold value is selected based on experimental results. In another embodiment, all of the paths are ranked based on interestingness.

A meaningful path may not necessarily be interesting, for example, if a highly ranked meaningful path is well known among biologists, it is likely no longer interesting. The approach captures this intuition using two matrices. (1) paths formed with hubs are less interesting, and (2) a path formed by multiple sources are more interesting.

If a node has significant number of incoming and outgoing links in the knowledge graph, this is a indication that this is a well-studied entity. Hence, it is less-likely that a interesting path exist through this node. Therefore, those paths are ranked lower in interesting measure. We call this the rarity of the path and this intuition is captured by the following equation:

Rarity(path)=$\pi n \epsilon path(1−(degree(n)/maxDeg))$ where, n is a node in the path, degree(n) is the number of incoming and outgoing edges of n. maxDeg is the degree of the node with maximum incoming and outgoing edges from the selected set of paths (paths that exceed threshold value of meaningfulness value).

In the second matrix, (2) a path formed by multiple sources are more interesting, such paths are found as follows. A path is formed by multiple nodes, if all of these nodes reside in a single source (e.g., one scientific article, etc.), that path is less interesting. Hence, the approach ranks paths that are formed by the facts extracted from multiple sources higher. This is referred to as 'source diversity' of the path. Source diversity is calculated as shown below:

source diversity=(number of edges with distinct documents)/(number of edges)

The final set of paths are ranked based on the average of the rarity of the path and the source diversity of the path. This ranked set of paths are then provided to a user of the system, such as a biological researcher, to more quickly and more easily identify meaningful and interesting areas of biology for further research and exploration. A scenario demonstrating why the process provided herein of identifying biological areas that are meaningful and interesting is provided below.

Imagine a biologist needs to find the paths that connects gene 'IL-6' and condition 'Cutaneous Melanoma'. We found genes like AKT1, TP53, IL1A connect these two entities (i.e., IL-6 interacts with AKT1 and AKT1 interacts with Cutaneous Melanoma). However, these genes are very popular and have high degree values (typically they connect to almost every gene in the network, hence less informative). For example, in this particular scenario we found that there are 50 distinct paths that connects IL-6 to Cutaneous Melanoma through AKT1 due to its high degree value.

On the other hand, gene WNT5A also connects IL-6 to Cutaneous Melanoma and there are only 9 such paths due to its low degree value. In fact, if we are to order the entities that connects IL-6 to Cutaneous Melanoma in descending order of the number of distinct paths, the paths through WNT5A appears in 26th position. However, we found the path that connects IL-6 to Cutaneous Melanoma through WNT5A particularly interesting and it is found to be a credible path.

Note that all of these paths already has diversity=1 (i.e., the interaction between IL-6 and Cutaneous Melanoma is not reported in a single document, hence, not known to the scientists). The features like rarity and diversity introduced in this approach ranks such paths higher than the other (more common) paths. Such ranking provides the researcher with possible fruitful paths to utilize in performing further research and discovery.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions. The following detailed description will generally follow the summary of the disclosure, as set forth above, further explaining and expanding the definitions of the various aspects and embodiments of the disclosure as necessary.

FIG. 1 depicts a schematic diagram of one illustrative embodiment of a question/answer (QA) system 100 in a computer network 102. QA system 100 may include knowledge manager 104, which comprises one or more processors and one or more memories, and potentially any other computing device elements generally known in the art including buses, storage devices, communication interfaces, and the like. Computer network 102 may include other computing devices in communication with each other and with other devices or components via one or more wired and/or wireless data communication links, where each communication link may comprise one or more of wires, routers, switches, transmitters, receivers, or the like. QA system 100 and network 102 may enable question/answer (QA) generation functionality for one or more content users. Other embodiments may include QA system 100 interacting with components, systems, sub-systems, and/or devices other than those depicted herein.

QA system 100 may receive inputs from various sources. For example, QA system 100 may receive input from the network 102, a corpus of electronic documents 107 or other data, semantic data 108, and other possible sources of input. In one embodiment, some or all of the inputs to QA system 100 route through the network 102 and stored in knowledge base 106. The various computing devices on the network 102 may include access points for content creators and content users. Some of the computing devices may include devices for a database storing the corpus of data. The network 102 may include local network connections and remote connections in various embodiments, such that QA system 100 may operate in environments of any size, including local and global, e.g., the Internet. Additionally, QA system 100 serves as a front-end system that can make available a variety of knowledge extracted from or represented in documents, network-accessible sources and/or structured data sources. In this manner, some processes populate the knowledge manager with the knowledge manager also including input interfaces to receive knowledge requests and respond accordingly.

In one embodiment, a content creator creates content in a document 107 for use as part of a corpus of data with QA system 100. The document 107 may include any file, text, article, or source of data for use in QA system 100. Content users may access QA system 100 via a network connection or an Internet connection to the network 102, and may input questions to QA system 100, which QA system 100 answers according to the content in the corpus of data. As further described below, when a process evaluates a given section of a document for semantic content, the process can use a variety of conventions to query it from knowledge manager 104. One convention is to send a well-formed question.

Semantic data 108 is content based on the relation between signifiers, such as words, phrases, signs, and symbols, and what they stand for, their denotation, or connotation. In other words, semantic data 108 is content that interprets an expression, such as by using Natural Language Processing (NLP). In one embodiment, the process sends well-formed questions (e.g., natural language questions, etc.) to QA system 100 and QA system 100 may interpret the question and provide a response that includes one or more answers to the question. In some embodiments, QA system 100 may provide a response to users in a ranked list of answers.

In some illustrative embodiments, QA system 100 may be the IBM Watson™ QA system available from International Business Machines Corporation of Armonk, N.Y., which is augmented with the mechanisms of the illustrative embodiments described hereafter. The IBM Watson™ knowledge manager system may receive an input question which it then parses to extract the major features of the question, that in turn are then used to formulate queries that are applied to the corpus of data. Based on the application of the queries to the corpus of data, a set of hypotheses, or candidate answers to the input question, are generated by looking across the corpus of data for portions of the corpus of data that have some potential for containing a valuable response to the input question.

The IBM Watson™ QA system then performs deep analysis on the language of the input question and the language used in each of the portions of the corpus of data found during the application of the queries using a variety of reasoning algorithms. There may be hundreds or even thousands of reasoning algorithms applied, each of which performs different analysis, e.g., comparisons, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm performed at establishing the inference between two similar passages for a particular domain during the training period of the IBM Watson™ QA system. The statistical model may then be used to summarize a level of confidence that the IBM Watson™ QA system has regarding the evidence that the potential response, i.e. candidate answer, is inferred by the question. This process may be repeated for each of the candidate answers until the IBM Watson™ QA system identifies candidate answers that surface as being significantly stronger than others and thus, generates a final answer, or ranked set of answers, for the input question. More information about the IBM Watson™ QA system may be obtained, for example, from the IBM Corporation website, IBM Redbooks, and the like. For example, information about the IBM Watson™ QA system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

Types of information handling systems that can utilize QA system 100 range from small handheld devices, such as handheld computer/mobile telephone 110 to large mainframe systems, such as mainframe computer 170. Examples of handheld computer 110 include personal digital assistants (PDAs), personal entertainment devices, such as MP3 players, portable televisions, and compact disc players. Other examples of information handling systems include pen, or tablet, computer 120, laptop, or notebook, computer 130, personal computer system 150, and server 160. As shown, the various information handling systems can be networked together using computer network 102. Types of computer network 102 that can be used to interconnect the various information handling systems include Local Area Networks (LANs), Wireless Local Area Networks (WLANs), the Internet, the Public Switched Telephone Network (PSTN), other wireless networks, and any other network topology that can be used to interconnect the information handling systems. Many of the information handling systems include nonvolatile data stores, such as hard drives and/or nonvolatile memory. Some of the information handling systems shown in FIG. 1 depicts separate nonvolatile data stores (server 160 utilizes nonvolatile data store 165, and mainframe computer 170 utilizes nonvolatile data store 175. The nonvolatile data store can be a component that is external to the various information handling systems or can be internal to one of the information handling systems. An illustrative example of an information handling system showing an exemplary processor and various components commonly accessed by the processor is shown in FIG. 2.

Figure 2:
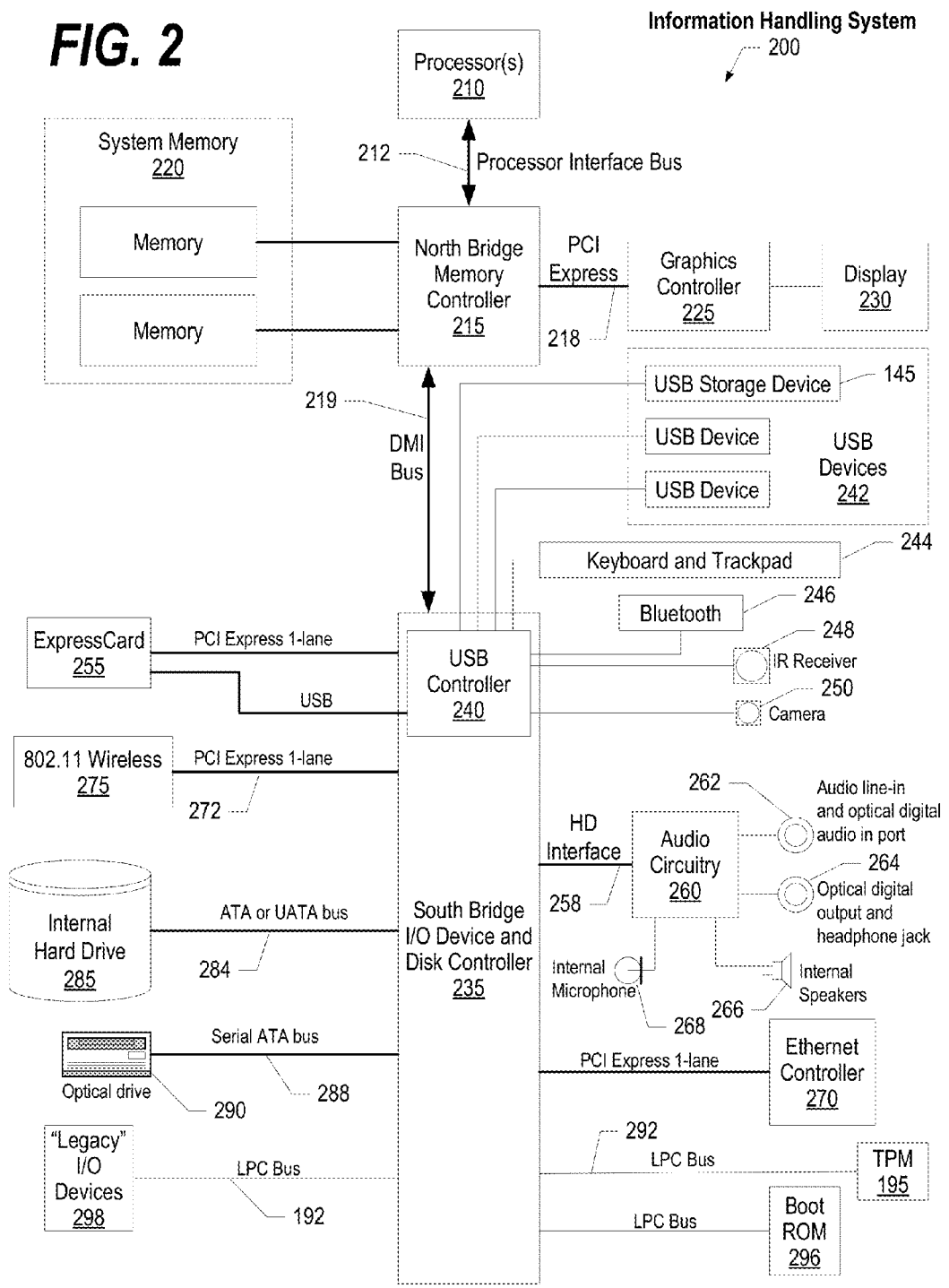
FIG. 2 illustrates an information handling system, more particularly, a processor and common components, which is a simplified example of a computer system capable of performing the computing operations described herein.

FIG. 2 illustrates information handling system 200, more particularly, a processor and common components, which is a simplified example of a computer system capable of performing the computing operations described herein. Information handling system 200 includes one or more processors 210 coupled to processor interface bus 212. Processor interface bus 212 connects processors 210 to Northbridge 215, which is also known as the Memory Controller Hub (MCH). Northbridge 215 connects to system memory 220 and provides a means for processor(s) 210 to access the system memory. Graphics controller 225 also connects to Northbridge 215. In one embodiment, PCI Express bus 218 connects Northbridge 215 to graphics controller 225. Graphics controller 225 connects to display device 230, such as a computer monitor.

Northbridge 215 and Southbridge 235 connect to each other using bus 219. In one embodiment, the bus is a Direct Media Interface (DMI) bus that transfers data at high speeds in each direction between Northbridge 215 and Southbridge 235. In another embodiment, a Peripheral Component Interconnect (PCI) bus connects the Northbridge and the Southbridge. Southbridge 235, also known as the I/O Controller Hub (ICH) is a chip that generally implements capabilities that operate at slower speeds than the capabilities provided by the Northbridge. Southbridge 235 typically provides various busses used to connect various components. These busses include, for example, PCI and PCI Express busses, an ISA bus, a System Management Bus (SMBus or SMB), and/or a Low Pin Count (LPC) bus. The LPC bus often connects low-bandwidth devices, such as boot ROM 296 and "legacy" I/O devices (using a "super I/O" chip). The "legacy" I/O devices (298) can include, for example, serial and parallel ports, keyboard, mouse, and/or a floppy disk controller. The LPC bus also connects Southbridge 235 to Trusted Platform Module (TPM) 295. Other components often included in Southbridge 235 include a Direct Memory Access (DMA) controller, a Programmable Interrupt Controller (PIC), and a storage device controller, which connects Southbridge 235 to nonvolatile storage device 285, such as a hard disk drive, using bus 284.

ExpressCard 255 is a slot that connects hot-pluggable devices to the information handling system. ExpressCard 255 supports both PCI Express and USB connectivity as it connects to Southbridge 235 using both the Universal Serial Bus (USB) the PCI Express bus. Southbridge 235 includes USB Controller 240 that provides USB connectivity to devices that connect to the USB. These devices include webcam (camera) 250, infrared (IR) receiver 248, keyboard and trackpad 244, and Bluetooth device 246, which provides for wireless personal area networks (PANs). USB Controller 240 also provides USB connectivity to other miscellaneous USB connected devices 242, such as a mouse, removable nonvolatile storage device 245, modems, network cards, ISDN connectors, fax, printers, USB hubs, and many other types of USB connected devices. While removable nonvolatile storage device 245 is shown as a USB-connected device, removable nonvolatile storage device 245 could be connected using a different interface, such as a Firewire interface, etcetera.

Wireless Local Area Network (LAN) device 275 connects to Southbridge 235 via the PCI or PCI Express bus 272. LAN device 275 typically implements one of the IEEE 0.802.11 standards of over-the-air modulation techniques that all use the same protocol to wireless communicate between information handling system 200 and another computer system or device. Optical storage device 290 connects to Southbridge 235 using Serial ATA (SATA) bus 288. Serial ATA adapters and devices communicate over a high-speed serial link. The Serial ATA bus also connects Southbridge 235 to other forms of storage devices, such as hard disk drives. Audio circuitry 260, such as a sound card, connects to Southbridge 235 via bus 258. Audio circuitry 260 also provides functionality such as audio line-in and optical digital audio in port 262, optical digital output and headphone jack 264, internal speakers 266, and internal microphone 268. Ethernet controller 270 connects to Southbridge 235 using a bus, such as the PCI or PCI Express bus. Ethernet controller 270 connects information handling system 200 to a computer network, such as a Local Area Network (LAN), the Internet, and other public and private computer networks.

While FIG. 2 shows one information handling system, an information handling system may take many forms, some of which are shown in FIG. 1. For example, an information handling system may take the form of a desktop, server, portable, laptop, notebook, or other form factor computer or data processing system. In addition, an information handling system may take other form factors such as a personal digital assistant (PDA), a gaming device, ATM machine, a portable telephone device, a communication device or other devices that include a processor and memory.

Figure 3:
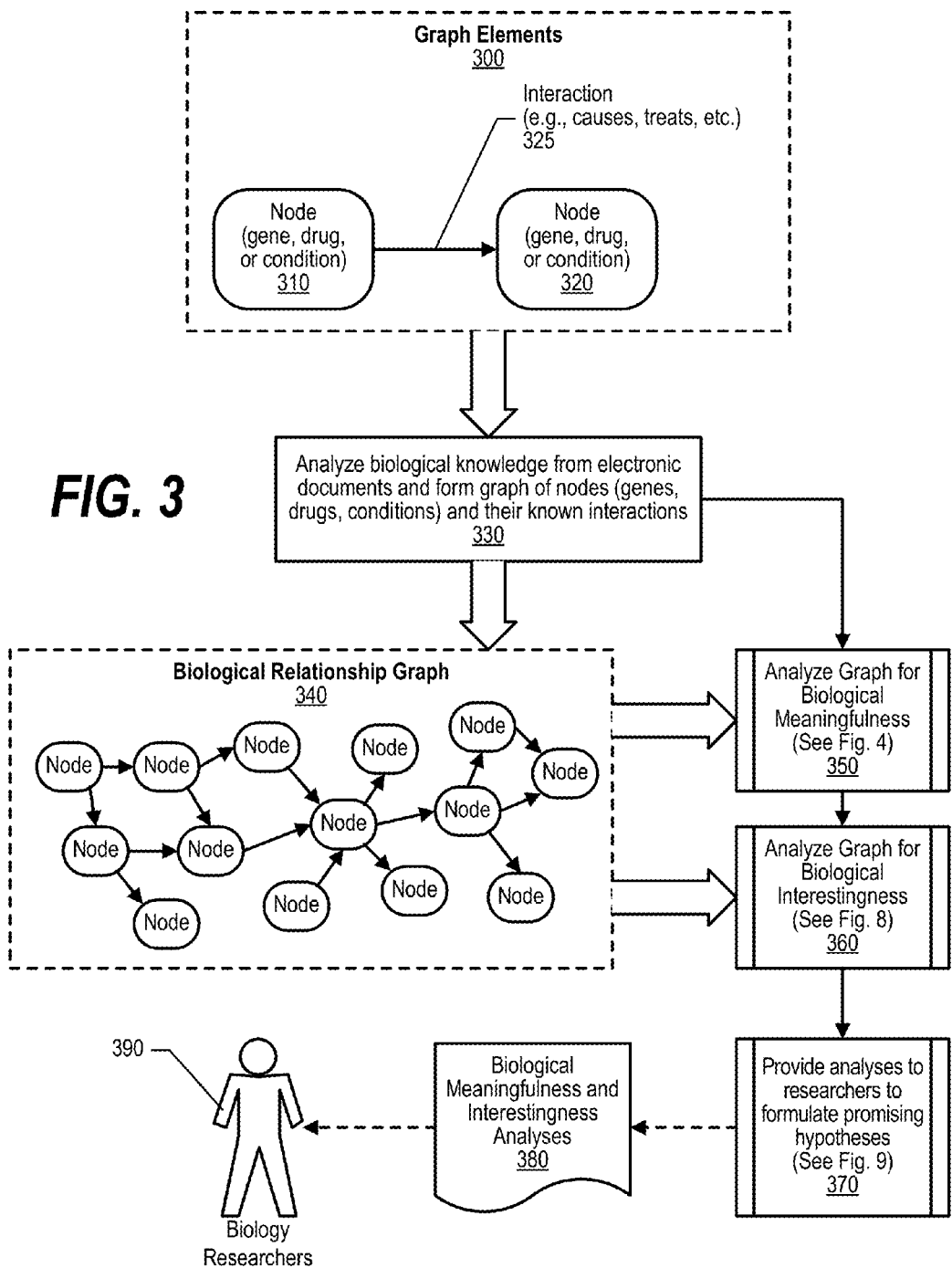
FIG. 3 is a high level diagram depicting the various components used in generating a biological meaningfulness and interestingness analysis.

FIG. 3 is a high level diagram depicting the various components used in generating a biological meaningfulness and interestingness analysis. The approach described herein identifies important paths in biological relationship graph 340 for exploration by researchers 390. Biological relationship graph 340 includes any number of nodes that are connected to each other to form paths through the graphs. As shown in graph elements depiction 300, any node 310 can be a biological element such as a gene, a drug, or a condition. Connection 325 between two nodes indicates an interaction between the two nodes, such as indicating that one node "causes" the other node, "treats" the other node, etc.

In the approach, a biological meaningfulness analysis is performed on the biological relationship graph that has a number of paths through the graph formed by a number of connected nodes. Predefined process 350 performs the biological meaningfulness analysis which is based on a process similarity calculation of gene ontologies of the nodes in the paths and a contextual similarity calculation of word occurrences from documents in a corpus where a reference to the respective nodes are found (see FIG. 4 and corresponding text for processing details).

A biological interestingness analysis is also performed on the biological relationship graph. Predefined process 360 performs the biological interestingness analysis which is based on a path diversity value calculated for each of the paths and a path rarity value calculated for each of the paths. The path diversity value is based on a number of distinct documents in each of the paths and the number of connections in the respective paths, while the path rarity value is based a total degrees of the nodes that form the paths. See FIG. 8 and corresponding text for processing details regarding the performance of the biological interestingness analysis.

The paths are then screened based on the biological meaningfulness analysis and the biological interestingness analysis. Predefined process 370 screens the data to identify meaningful and interesting paths through the biological relationship graph. These meaningful and interesting paths are displayed to user 390, such as a biology researcher, in display 380, such as a report, in order to assist the researcher in formulating promising hypotheses that can be explored and researched to make new discoveries in the biological sciences.

Figure 4:
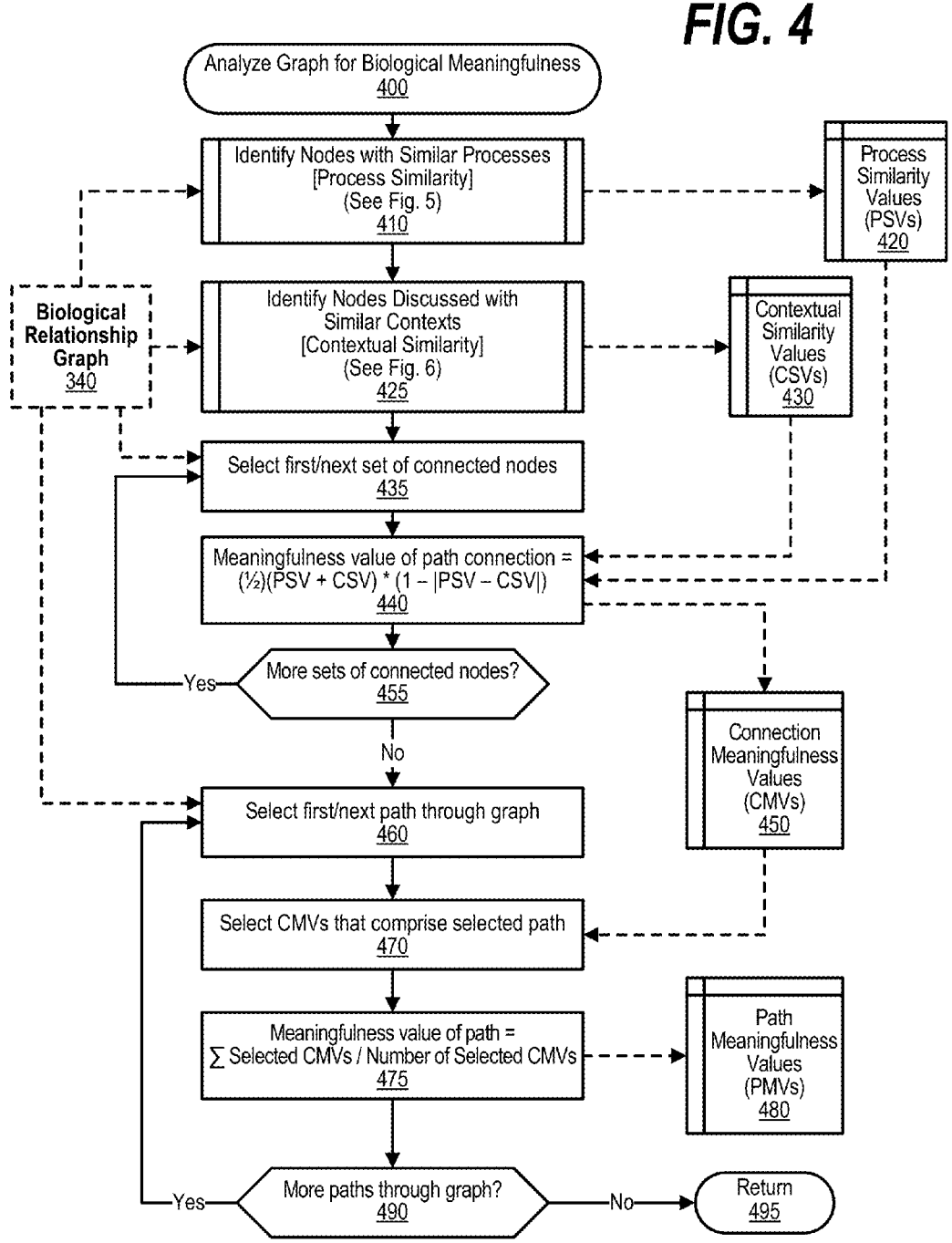
FIG. 4 is a flowchart showing steps performed to analyze a biological relationship graph for biological meaningfulness.

FIG. 4 is a flowchart showing steps performed to analyze a biological relationship graph for biological meaningfulness. FIG. 4 processing commences at 400 and shows the steps taken by a process that analyzes biological relationship graph data store 340 for biological meaningfulness. At predefined process 410, the process performs the Identify Nodes with Similar Processes [Process Similarity] routine (see FIG. 5 and corresponding text for processing details). The results of predefined process 410 are process similarity values (PSVs) that are stored in memory area 420.

Figure 6:
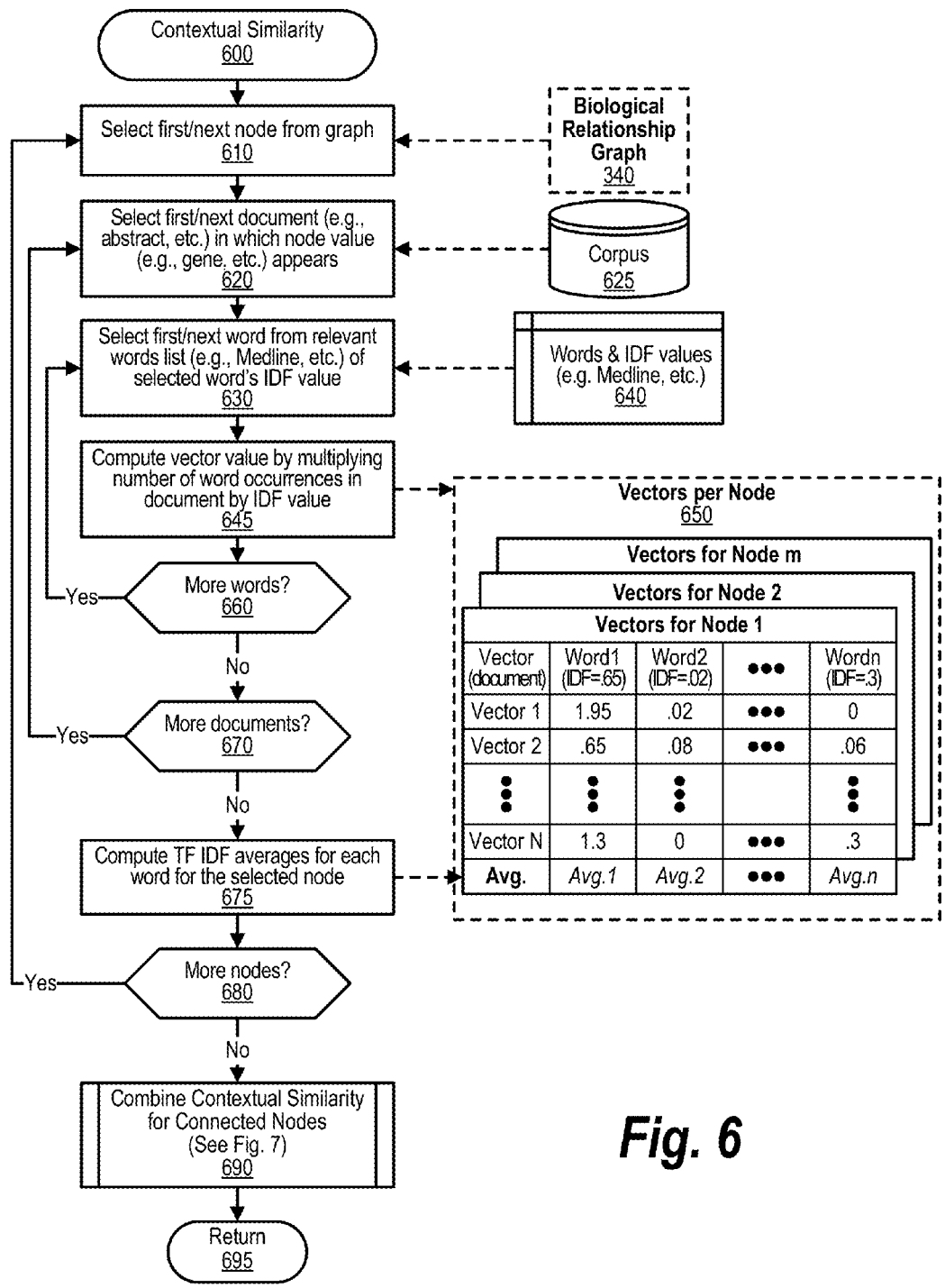
FIG. 6 is a flowchart showing steps performed to analyze nodes for contextual similarity.

At predefined process 425, the process performs the Identify Nodes Discussed with Similar Contexts [Contextual Similarity] routine (see FIG. 6 and corresponding text for processing details). The results of predefined process 425 are contextual similarity values (CSVs) that are stored in memory area 430.

At step 435, the process selects the first set of connected nodes from Biological Relationship Graph 340. At step 440, the process calculates a connection meaningfulnesss value (CMV) for the selected path connection. in one embodiment, the CMV is calculated as being equal to (½)(PSV+CSV)*(1−|PSV−CSV|). The CMVs that are calculated for each of the sets of connected nodes are stored in memory area 450. The process determines as to whether there are more sets of connected nodes in Biological Relationship Graph 340 to process (decision 455). If there are more sets of connected nodes to process, then decision 455 branches to the 'yes' branch which loops back to step 435 to select the next set of connected nodes and calculate its meaningfulness value as described above. This looping continues there are no more sets of connected nodes to select, at which point decision 455 branches to the 'no' branch exiting the loop.

At step 460, the process selects the first path through Biological Relationship Graph 340. At step 470, the process selects the CMVs that comprise the selected path. The CMVs for the selected path are retrieved from memory area 450. At step 475, the process calculates the path meaningfulness value (PMV) corresponding to the selected path. in one embodiment, the PMV is calculated as being equal to Σ Selected CMVs/Number of Selected CMVs. The process determines as to whether there are more paths through Biological Relationship Graph 340 that need to be processed (decision 490). If there are more paths through graph to process, then decision 490 branches to the 'yes' branch which loops back to step 460 to select and process the next path through the graph. This looping continues until all of the paths have been processed, at which point decision 490 branches to the 'no' branch exiting the loop. FIG. 4 processing thereafter returns to the calling routine (see FIG. 3) at 495.

Figure 5:
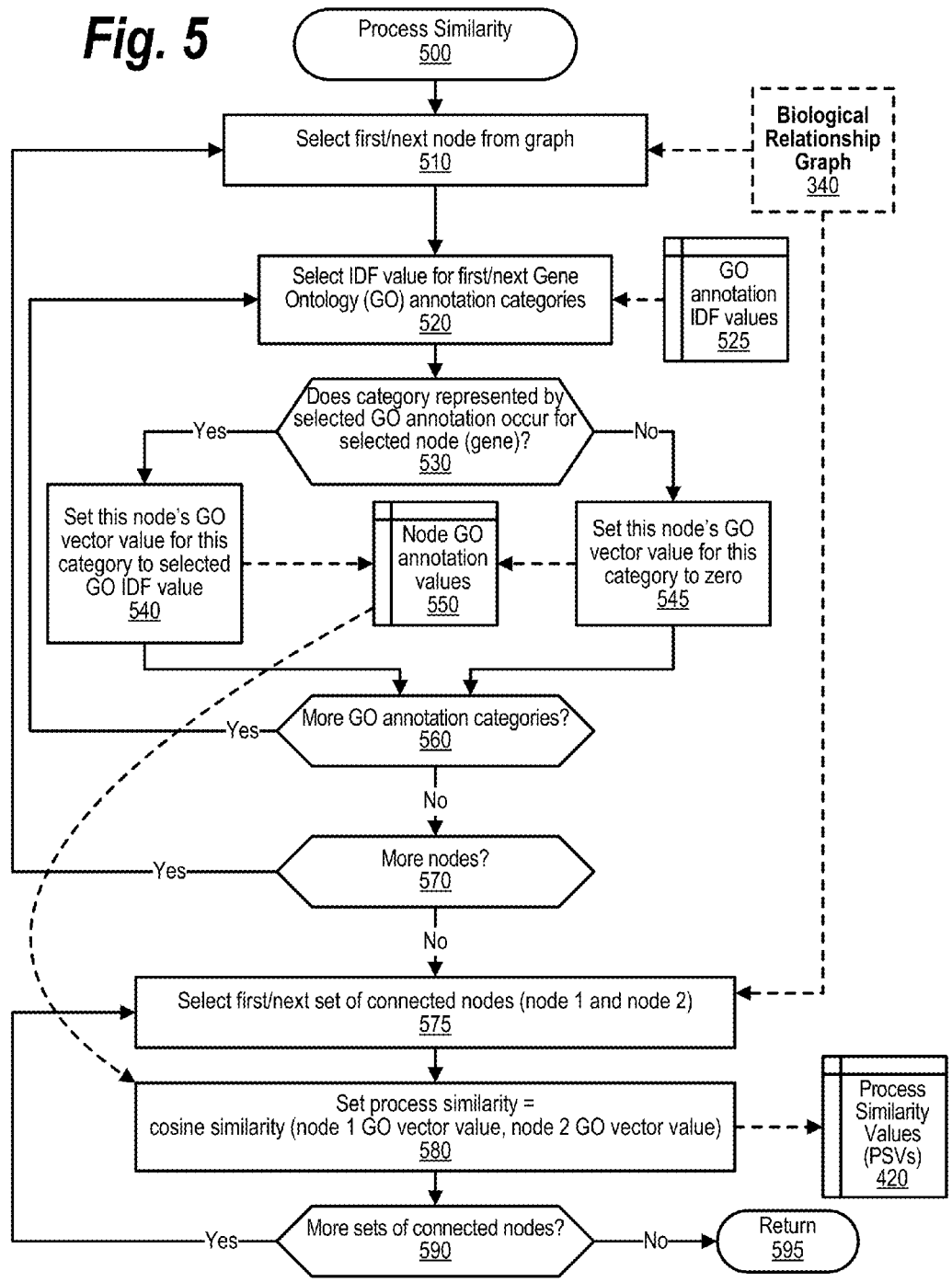
FIG. 5 is a flowchart showing steps performed to analyze nodes for process similarity.

FIG. 5 is a flowchart showing steps performed to analyze nodes for process similarity. FIG. 5 processing commences at 500 and shows the steps taken by a process that analyzes the process similarity of nodes in the Biological Relationship Graph. At step 510, the process selects the first node from Biological Relationship Graph 340. At step 520, the process selects the IDF value for the first Gene Ontology (GO) annotation category from memory area 525. Memory area 525 includes the GO annotation IDF values for numerous biological categories.

At decision 530, the process determines whether the category that is represented by the selected GO annotation occurs for the selected node (e.g., gene, etc.). If the category that is represented by the selected GO annotation occurs for the selected node, then decision 530 branches to the 'yes' branch to perform step 540. On the other hand, if the category that is represented by the selected GO annotation does not occur for the selected node, then decision 530 branches to the 'no' branch to perform step 545. At step 540, the process sets the selected node's GO vector value for this category to the selected GO annotation IDF value. At step 545, the process sets this node's GO vector value for this category to zero. The node's GO vector value is stored in memory area 550.

The process determines whether there are more GO annotation categories to process for the selected node (decision 560). If there are more GO annotation categories to process for the selected node, then decision 560 branches to the 'yes' branch which loops back to step 520 to select the next IDF value from memory area 525 and repeat the processing described above. This looping continues until there are no more GO annotation categories to process for the selected node, at which point decision 560 branches to the 'no' branch exiting the loop. The process next determines whether there are more nodes in the Biological Relationship Graph to process (decision 570). If there are more nodes to process, then decision 570 branches to the 'yes' branch which loops back to step 510 and repeats the processing described above. This looping continues until there are no more nodes to process, at which point decision 570 branches to the 'no' branch exiting the loop.

At step 575, the process selects the first set of connected nodes (node 1 and node 2) from Biological Relationship Graph 340. At step 580, the process sets the process similarity value (PSV) of the selected connection to be the cosine similarity of the two node's vector values (cosine similarity (node 1 GO vector value, node 2 GO vector value). The process determines as to whether there are more sets of connected nodes to process (decision 590). If there are more sets of connected nodes to process, then decision 590 branches to the 'yes' branch which loops back to step 575 to select and process the next set of connected nodes from Biological Relationship Graph 340 as described above. This looping continues until there are no more connections to process, at which point decision 590 branches to the 'no' branch exiting the loop. FIG. 5 processing thereafter returns to the calling routine (see FIG. 4) at 595.

FIG. 6 is a flowchart showing steps performed to analyze nodes for contextual similarity. FIG. 6 processing commences at 600 and shows the steps taken by a process that analyzes the contextual similarity of nodes found in Biological Relationship Graph 340. At step 610, the process selects the first node from Biological Relationship Graph 340. At step 620, the process selects the first document (e.g., abstract, etc.) in which the selected node representation (e.g., gene, etc.) appears. At step 630, the process selects the first word from the relevant words list (e.g., Medline, etc.) and retrieves the selected word's inverse document frequency (IDF) value. The relevant (e.g., biologically significant, etc.) words and their IDF values is retrieved from memory area 640.

At step 645, the process computes a vector value for the node by multiplying the number of occurrences of the selected word in the selected document by the retrieved IDF value. The vectors for a node are stored in memory area 650. In memory area 650, each node is represented by a table of vector values. Each vector in the table corresponds to a document in which the node was found, with the vector values for each value being the results of the word analysis with the number of times each word occurs multiplied by its respective IDF value.

The process determines as to whether there are more words in memory area 640 to process (decision 660). If there are more words to process, then decision 660 branches to the 'yes' branch which loops back to step 630 to select and process the next word as described above. This looping continues until there are no more words to select, at which point decision 660 branches to the 'no' branch exiting the loop. The process next determines whether there are more documents from corpus 625 to select and process (decision 670). If there are more documents to select and process, then decision 670 branches to the 'yes' branch which loops back to step 620 to select the next document from corpus 625 and process the words in the document as described above. This looping continues until there are no more documents to process, at which point decision 670 branches to the 'no' branch exiting the loop.

At step 675, the process computes the term frequency-inverse document frequency (TF-IDF) averages for each word included in the table for the selected node. The process determines whether there are more nodes in Biological Relationship Graph 340 to process (decision 680). If there are more nodes to process, then decision 680 branches to the 'yes' branch which loops back to step 610 to select the next node from Biological Relationship Graph 340 and process the node as described above. This looping continues until there are no more nodes to process, at which point decision 680 branches to the 'no' branch exiting the loop. At predefined process 690, the process performs the Combine Contextual Similarity for Connected Nodes routine (see FIG. 7 and corresponding text for processing details). FIG. 6 processing thereafter returns to the calling routine (see FIG. 4) at 695.

Figure 7:
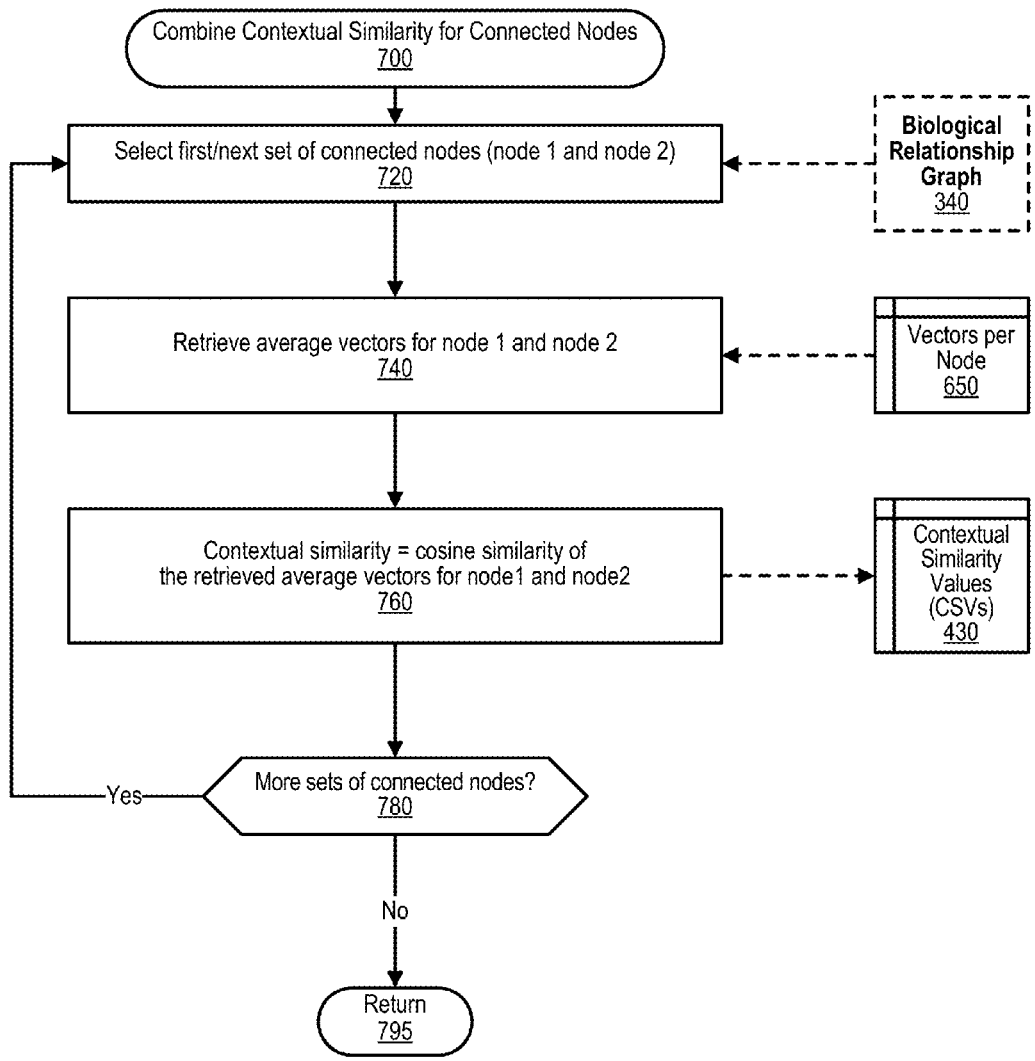
FIG. 7 is a flowchart showing steps performed to combine contextual similarity for connected nodes.

FIG. 7 is a flowchart showing steps performed to combine contextual similarity for connected nodes. FIG. 7 processing commences at 700 and shows the steps taken by a process that combines the contextual similarity values for sets of connected nodes. At step 720, the process selects the first set of connected nodes (node 1 and node 2) from Biological Relationship Graph 340.

At step 740, the process retrieves the average vector values for both node 1 and node 2. The average vector values were computed in the process shown in FIG. 6 and are retrieved from memory area 650. At step 760, the process computes the contextual similarity value (CSV) of the selected connection. in one embodiment, the CSV is calculated as being equal to the cosine similarity of the retrieved average vectors for node 1 and node 2. The calculated CSV for the connection is stored in memory area 430.

The process determines whether there are more sets of connected nodes from Biological Relationship Graph 340 to select and process as described above (decision 780). If there are more sets of connected nodes to select and process, then decision 780 branches to the 'yes' branch which loops back to step 720 to select and process the next set of connected nodes from Biological Relationship Graph 340. This looping continues until there are no more sets of connected nodes to process, at which point decision 780 branches to the 'no' branch exiting the loop. FIG. 7 processing thereafter returns to the calling routine (see FIG. 6) at 795.

Figure 8:
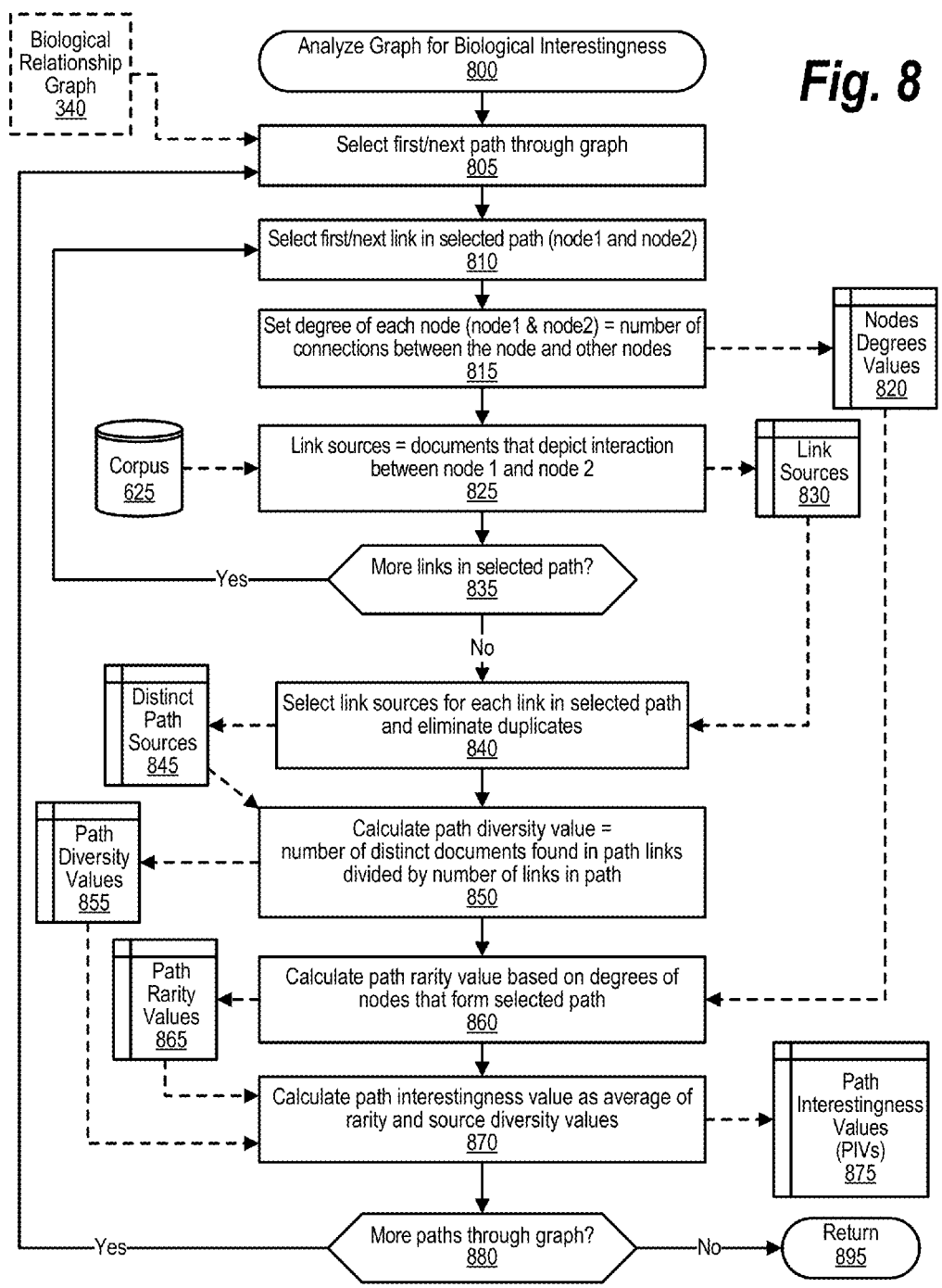
FIG. 8 is a flowchart showing steps performed to analyze a biological relationship graph for biological interestingness.

FIG. 8 is a flowchart showing steps performed to analyze a biological relationship graph for biological interestingness. FIG. 8 processing commences at 800 and shows the steps taken by a process that analyzes Biological Relationship Graph 340 for biological interestingness. At step 805, the process selects the first path through Biological Relationship Graph 340. At step 810, the process selects the first connection, or link, in the selected path (node 1 connected to node 2).

At step 815, the process sets the degree of each node (node 1 and node 2) to be the number of connections between the respective node and other nodes in Biological Relationship Graph 340. For example, if node 1 has five connections with other nodes and node 2 has three connections, then the degree of node 1 would be set to five and the degree of node 2 would be set to three. At step 825, the process identifies link data sources as being documents from corpus 625 that depict at least one interaction between node 1 and node 2. The identifiers of these link sources (e.g., title, etc.) are stored in memory area 830.

The process determines whether there are more connections in the selected path that need to be selected and processed (decision 835). If there are more connections in the selected path, then decision 835 branches to the 'yes' branch which loops back to step 810 to select the next connection (another node 1 and node 2) and process the next connection as described above. This looping continues until there are no more links in the selected path to process, at which point decision 835 branches to the 'no' branch exiting the loop.

At step 840, the process selects the link sources corresponding to each link that was identified in the selected path (stored in memory area 830) and the process eliminates duplicate entries from the list of link sources. These distinct path sources are stored in memory area 845. At step 850, the process calculates a path diversity value for the selected path. In one embodiment, the path diversity value is calculated as being equal to the number of distinct documents found in the selected path connections divided by the number of connections in the selected path. The path diversity values are stored in memory area 855.

At step 860, the process calculates a path rarity value for the selected path. in one embodiment, the path rarity value is calculated as being the total number of degrees from all of the nodes that form the selected path. The path rarity values are stored in memory area 865. At step 870, the process calculates the path interestingness value (PIV) for the selected path. in one embodiment, the PIV is calculated as being the average of the path's rarity value and the path's source diversity values with the respective values being retrieved from memory areas 855 and 865, and the PIVs being stored in memory area 875.

The process determines whether there are more paths through Biological Relationship Graph 340 left to process (decision 880). If there are more paths to process, then decision 880 branches to the 'yes' branch which loops back to step 805 to select and process the next path for biological interestingness. This looping continues until there are no more paths from Biological Relationship Graph 340 to select and process, at which point decision 880 branches to the 'no' branch exiting the loop. FIG. 8 processing thereafter returns to the calling routine (see FIG. 3) at 895.

Figure 9:
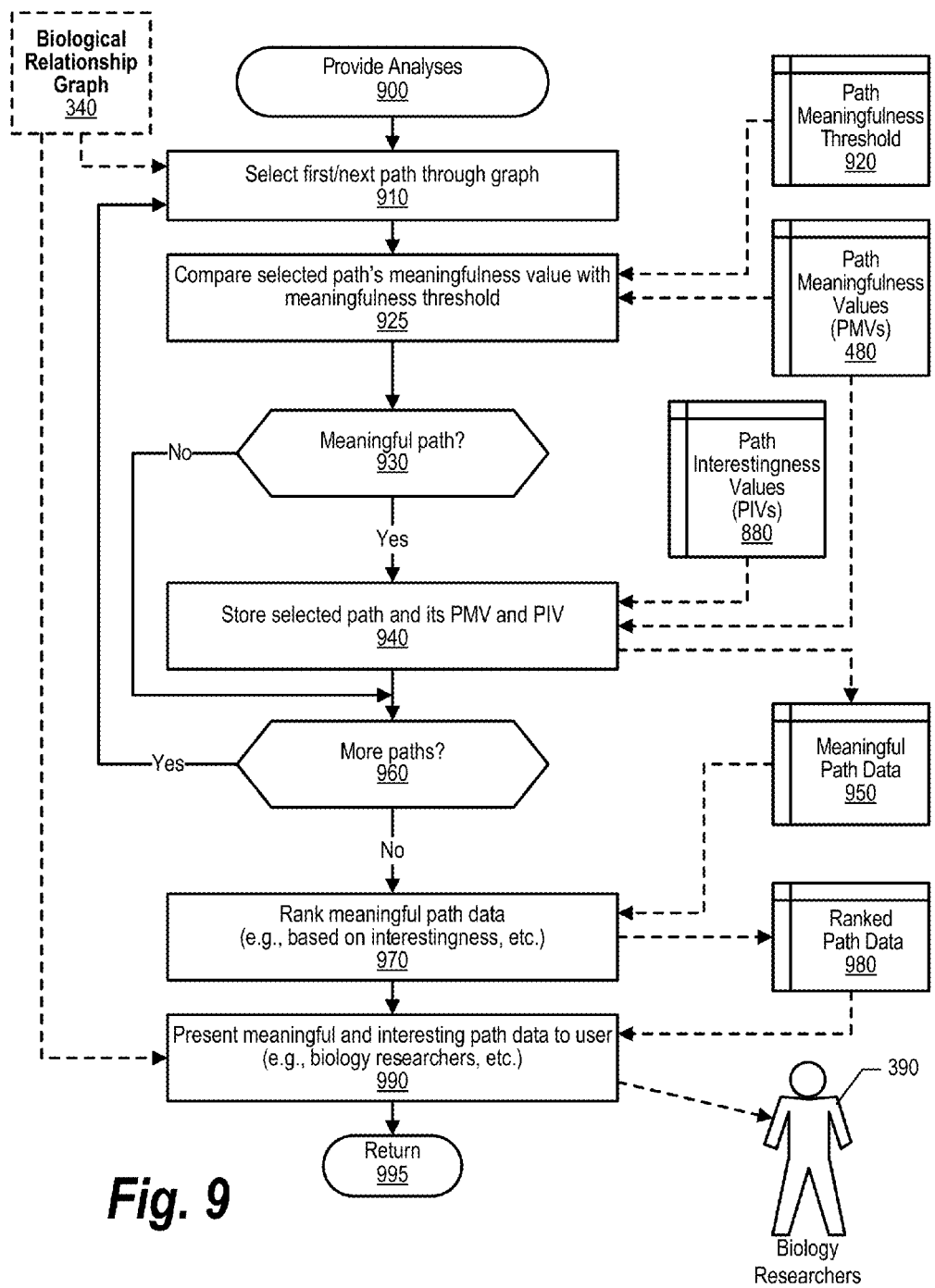
FIG. 9 is flowchart showing steps performed to provide a biological meaningfulness and interestingness analysis to a user of the system.

FIG. 9 is flowchart showing steps performed to provide a biological meaningfulness and interestingness analysis to a user of the system, such as a biology researcher. FIG. 9 processing commences at 900 and shows the steps taken by a process that provides the analyses of Biological Relationship Graph 340 to a user. At step 910, the process selects the first path through Biological Relationship Graph 340.

At step 925, the process compares the selected path's meaningfulness value, retrieved from memory area 480, with a meaningfulness threshold that has been set for the analysis. The meaningfulness threshold is retrieved from memory area 920. Based on the comparison, the process determines whether the selected path is a meaningful path (decision 930). If the selected path is a meaningful path, then decision 930 branches to the 'yes' branch to perform step 940. On the other hand, if the selected path is not a meaningful path, then decision 930 branches to the 'no' branch bypassing step 940. At step 940, the process stores the selected path and its path meaningfulness value (PMV) and path interestingness value (PIV) in memory area 950.

The process determines whether there are more paths from Biological Relationship Graph 340 to process (decision 960). If there are more paths to process, then decision 960 branches to the 'yes' branch which loops back to step 910 to select and process the next path through Biological Relationship Graph 340. This looping continues until there are no more paths to process, at which point decision 960 branches to the 'no' branch exiting the loop.

At step 970, the process ranks the meaningful path data. in one embodiment, the ranking is based on the respective paths' interestingness values (PIVs). The ranked path data is stored in memory area 980. At step 990, the process retrieves the ranked meaningful and interesting path data from memory area 980 and presents the path data to user 390 (e.g., biology researchers, etc.). User 390 can then further explore and analyze the interesting and meaningful paths to formulate more biology hypotheses. FIG. 9 processing thereafter returns to the calling routine (see FIG. 3) at 995.

While particular embodiments of the present disclosure have been shown and described, it will be obvious to those skilled in the art that, based upon the teachings herein, that changes and modifications may be made without departing from this disclosure and its broader aspects. Therefore, the appended claims are to encompass within their scope all such changes and modifications as are within the true spirit and scope of this disclosure. Furthermore, it is to be understood that the disclosure is solely defined by the appended claims. It will be understood by those with skill in the art that if a specific number of an introduced claim element is intended, such intent will be explicitly recited in the claim, and in the absence of such recitation no such limitation is present. For non-limiting example, as an aid to understanding, the following appended claims contain usage of the introductory phrases "at least one" and "one or more" to introduce claim elements. However, the use of such phrases should not be construed to imply that the introduction of a claim element by the indefinite articles "a" or "an" limits any particular claim containing such introduced claim element to disclosures containing only one such element, even when the same claim includes the introductory phrases "one or more" or "at least one" and indefinite articles such as "a" or "an"; the same holds true for the use in the claims of definite articles.

The invention claimed is:

1. A method implemented by an information handling system that includes a memory and a processor, the method comprising:

performing a biological meaningfulness analysis on a biological relationship graph that has a plurality of paths through the graph, wherein each of the plurality of paths includes a plurality of connected nodes, and wherein the biological meaningfulness analysis is based on a process similarity calculation of gene ontologies of the nodes in the paths and a contextual similarity calculation of word occurrences from a plurality of documents in a corpus where a reference to the respective nodes are found;

performing a biological interestingness analysis on the biological relationship graph that is based on a path diversity value calculated for each of the paths and a path rarity value calculated for each of the paths, wherein the path diversity value is based on a number of distinct documents in each of the paths and the number of connections in the respective paths, and wherein the path rarity value is based a total degrees of nodes that form each of the paths; and screening the plurality of paths in the biological relationship graph based on the biological meaningfulness analysis and the biological interestingness analysis, wherein the screened plurality of paths are displayed to a user, and wherein the screening further comprises:

identifying one or more meaningful paths through the biological relationship graph based on comparing a path meaningfulness value (PMV) with a threshold; and ranking the meaningful paths by a path interestingness value (PIV) corresponding to each of the meaningful paths.

2. The method of claim 1 wherein performing the biological meaningfulness analysis further comprises:

identifying a plurality of the nodes that exhibit one or more similar processes by:

selecting a plurality of gene ontology (GO) annotations;

setting a GO vector value for one or more nodes where the selected GO annotation occurs to a value based on an inverse document frequency (IDF) value corresponding to a biological category represented by each of the selected GO annotations; and calculating a process similarity value (PSV) corresponding to a plurality of connections between the plurality of nodes based on the GO vector values set for each of the nodes included in each of the connections.

3. The method of claim 1 wherein performing the biological meaningfulness analysis further comprises:
identifying a plurality of the nodes that exhibit a contextual similarity with each other by:
selecting a plurality of documents where the nodes appear in the corpus;
setting a plurality of word vector values corresponding to a plurality of biologically significant words for each the nodes based on a frequency that the biologically significant words appear in the same documents as each of the nodes;
calculating a plurality of term frequency-inverse document frequency (TFIDF) averages corresponding to each of the biologically significant words for each of the nodes; and
calculating a contextual similarity value (CSV) corresponding to a plurality of connections between the plurality of nodes by combining the TFIDF averages calculated for each of the nodes included in each of the connections.

4. The method of claim 3 further comprising:
calculating the CSV corresponding to the plurality of connections as being a cosine similarity of the TFIDF averages calculated for each of the nodes included in each of the connections.

5. The method of claim 1 wherein performing the biological interestingness analysis further comprises:
selecting each of the plurality of paths through the graph;
for each of the selected paths:
selecting each of the connections between the nodes that form the selected path;
setting a degree of each of the selected nodes included in the selected path to a number of connections between the selected node an other nodes in the graph; and
calculating the path rarity value as a total number of degrees included in all of the nodes that form the selected path.

6. The method of claim 1 wherein performing the biological interestingness analysis further comprises:
selecting each of the plurality of paths through the graph;
for each of the selected paths:
selecting each of the connections between the nodes that form the selected path;
for each of the selected connections, identifying a set of distinct link sources from the corpus that depict an interaction between the two nodes that form the selected connection; and
calculating the path diversity value as a total number of distinct documents found in the selected path divided by the number of connections in the selected path.

7. An information handling system comprising:
one or more processors;
one or more data stores accessible by at least one of the processors;
a memory coupled to at least one of the processors; and
a set of computer program instructions stored in the memory and executed by at least one of the processors in order to perform actions of:
performing a biological meaningfulness analysis on a biological relationship graph that has a plurality of paths through the graph, wherein each of the plurality of paths includes a plurality of connected nodes, and wherein the biological meaningfulness analysis is based on a process similarity calculation of gene ontologies of the nodes in the paths and a contextual similarity calculation of word occurrences from a plurality of documents in a corpus where a reference to the respective nodes are found;
performing a biological interestingness analysis on the biological relationship graph that is based on a path diversity value calculated for each of the paths and a path rarity value calculated for each of the paths, wherein the path diversity value is based on a number of distinct documents in each of the paths and the number of connections in the respective paths, and wherein the path rarity value is based a total degrees of nodes that form each of the paths; and
screening the plurality of paths in the biological relationship graph based on the biological meaningfulness analysis and the biological interestingness analysis, wherein the screened plurality of paths are displayed to a user, and wherein the screening further comprises actions of:
identifying one or more meaningful paths through the biological relationship graph based on comparing a path meaningfulness value (PMV) with a threshold; and
ranking the meaningful paths by a path interestingness value (PIV) corresponding to each of the meaningful paths.

8. The information handling system of claim 7 wherein performing the biological meaningfulness analysis further comprises actions of:
identifying a plurality of the nodes that exhibit one or more similar processes by:
selecting a plurality of gene ontology (GO) annotations;
setting a GO vector value for one or more nodes where the selected GO annotation occurs to a value based on an inverse document frequency (IDF) value corresponding to a biological category represented by each of the selected GO annotations; and
calculating a process similarity value (PSV) corresponding to a plurality of connections between the plurality of nodes based on the GO vector values set for each of the nodes included in each of the connections.

9. The information handling system of claim 7 wherein performing the biological meaningfulness analysis further comprises actions of:
identifying a plurality of the nodes that exhibit a contextual similarity with each other by:
selecting a plurality of documents where the nodes appear in the corpus;
setting a plurality of word vector values corresponding to a plurality of biologically significant words for each the nodes based on a frequency that the biologically significant words appear in the same documents as each of the nodes;
calculating a plurality of term frequency-inverse document frequency (TFIDF) averages corresponding to each of the biologically significant words for each of the nodes; and
calculating a contextual similarity value (CSV) corresponding to a plurality of connections between the plurality of nodes by combining the TFIDF averages calculated for each of the nodes included in each of the connections.

10. The information handling system of claim 9 wherein the actions further comprise:

calculating the CSV corresponding to the plurality of connections as being a cosine similarity of the TFIDF averages calculated for each of the nodes included in each of the connections.

11. The information handling system of claim 7 wherein performing the biological interestingness analysis further comprises actions of:
   selecting each of the plurality of paths through the graph;
   for each of the selected paths:
      selecting each of the connections between the nodes that form the selected path;
      setting a degree of each of the selected nodes included in the selected path to a number of connections between the selected node an other nodes in the graph; and
      calculating the path rarity value as a total number of degrees included in all of the nodes that form the selected path.

12. The information handling system of claim 7 wherein performing the biological interestingness analysis further comprises actions of:
   selecting each of the plurality of paths through the graph;
   for each of the selected paths:
      selecting each of the connections between the nodes that form the selected path;
      for each of the selected connections, identifying a set of distinct link sources from the corpus that depict an interaction between the two nodes that form the selected connection; and
      calculating the path diversity value as a total number of distinct documents found in the selected path divided by the number of connections in the selected path.

13. A computer program product stored in a computer readable storage medium, comprising computer program code that, when executed by an information handling system, causes the information handling system to perform actions comprising:
   performing a biological meaningfulness analysis on a biological relationship graph that has a plurality of paths through the graph, wherein each of the plurality of paths includes a plurality of connected nodes, and wherein the biological meaningfulness analysis is based on a process similarity calculation of gene ontologies of the nodes in the paths and a contextual similarity calculation of word occurrences from a plurality of documents in a corpus where a reference to the respective nodes are found;
   performing a biological interestingness analysis on the biological relationship graph that is based on a path diversity value calculated for each of the paths and a path rarity value calculated for each of the paths, wherein the path diversity value is based on a number of distinct documents in each of the paths and the number of connections in the respective paths, and wherein the path rarity value is based a total degrees of nodes that form each of the paths; and
   screening the plurality of paths in the biological relationship graph based on the biological meaningfulness analysis and the biological interestingness analysis, wherein the screened plurality of paths are displayed to a user, and wherein the screening further comprises actions of:
      identifying one or more meaningful paths through the biological relationship graph based on comparing a path meaningfulness value (PMV) with a threshold; and
      ranking the meaningful paths by a path interestingness value (PIV) corresponding to each of the meaningful paths.

14. The computer program product of claim 13 wherein performing the biological meaningfulness analysis further comprises actions of:
   identifying a plurality of the nodes that exhibit one or more similar processes by:
      selecting a plurality of gene ontology (GO) annotations;
      setting a GO vector value for one or more nodes where the selected GO annotation occurs to a value based on an inverse document frequency (IDF) value corresponding to a biological category represented by each of the selected GO annotations; and
      calculating a process similarity value (PSV) corresponding to a plurality of connections between the plurality of nodes based on the GO vector values set for each of the nodes included in each of the connections.

15. The computer program product of claim 13 wherein performing the biological meaningfulness analysis further comprises actions of:
   identifying a plurality of the nodes that exhibit a contextual similarity with each other by:
      selecting a plurality of documents where the nodes appear in the corpus;
      setting a plurality of word vector values corresponding to a plurality of biologically significant words for each the nodes based on a frequency that the biologically significant words appear in the same documents as each of the nodes;
      calculating a plurality of term frequency-inverse document frequency (TFIDF) averages corresponding to each of the biologically significant words for each of the nodes; and
      calculating a contextual similarity value (CSV) corresponding to a plurality of connections between the plurality of nodes by combining the TFIDF averages calculated for each of the nodes included in each of the connections.

16. The computer program product of claim 13 wherein performing the biological interestingness analysis further comprises actions of:
   selecting each of the plurality of paths through the graph;
   for each of the selected paths:
      selecting each of the connections between the nodes that form the selected path;
      setting a degree of each of the selected nodes included in the selected path to a number of connections between the selected node an other nodes in the graph; and
      calculating the path rarity value as a total number of degrees included in all of the nodes that form the selected path.

17. The computer program product of claim 13 wherein performing the biological interestingness analysis further comprises actions of:
   selecting each of the plurality of paths through the graph;
   for each of the selected paths:
      selecting each of the connections between the nodes that form the selected path;
      for each of the selected connections, identifying a set of distinct link sources from the corpus that depict an interaction between the two nodes that form the selected connection; and calculating the path diversity value as a total number of distinct documents found in the selected path divided by the number of connections in the selected path.

* * * * *